(12) United States Patent
Shaw et al.

(10) Patent No.: US 8,389,299 B2
(45) Date of Patent: Mar. 5, 2013

(54) PHOTONIC BIOSENSOR ARRAYS

(75) Inventors: Andrew Mark Shaw, Exeter (GB); Rouslan Vladamir Olkhov, Devonshire (GB); William Leslie Barnes, Devonshire (GB)

(73) Assignee: Attomarker Limited (GB)

( * ) Notice: Subject to any disclaimer, the term of this patent is extended or adjusted under 35 U.S.C. 154(b) by 370 days.

(21) Appl. No.: 12/531,814

(22) PCT Filed: Mar. 19, 2008

(86) PCT No.: PCT/GB2008/050202
§ 371 (c)(1),
(2), (4) Date: Jan. 26, 2010

(87) PCT Pub. No.: WO2008/117087
PCT Pub. Date: Oct. 2, 2008

(65) Prior Publication Data
US 2010/0167946 A1     Jul. 1, 2010

(30) Foreign Application Priority Data
Mar. 23, 2007 (GB) .................................. 0705594.0

(51) Int. Cl.
*G01N 33/53* (2006.01)

(52) U.S. Cl. ........ 436/809; 436/149; 436/164; 436/172; 436/174; 436/518; 436/805; 422/68.1; 422/82.05; 422/82.06; 422/82.08; 422/82.09; 422/82.11; 422/407; 435/164; 435/165; 435/283.1; 435/287.1; 435/287.2; 435/4; 435/5; 435/7.2; 435/7.9; 356/369; 506/9

(58) Field of Classification Search ................. 422/68.1, 422/82.05, 82.06, 82.08, 82.09, 82.11, 99, 422/40; 435/164, 165, 283.1, 287.1, 287.2, 435/4, 5, 7.2, 7.9; 436/149, 164, 172, 174, 436/518, 805, 809; 356/369; 506/9
See application file for complete search history.

(56) References Cited

U.S. PATENT DOCUMENTS 6,180,415 B1 * 1/2001 Schultz et al. ................ 436/518
(Continued)

FOREIGN PATENT DOCUMENTS

EP     1715326     10/2006

OTHER PUBLICATIONS

Hooper et al, "Differential ellipsometric surface plasmon resonance sensors with liquid crystal polarization modulators" Applied Physics Letters, vol. 85, No. 15, Oct. 11, 2004, p. 3017-3019.*

(Continued)

*Primary Examiner* — Dennis M White
(74) *Attorney, Agent, or Firm* — Snell & Wilmer L.L.P.

(57) ABSTRACT

This invention relates to photonic biosensor arrays in particular employing plasmon resonance based sensing, and to methods and apparatus for reading such arrays. A biosensor array for plasmon resonance-based sensing of a plurality of different biological targets simultaneously, the array comprising a transparent substrate having a surface bearing a plurality of assay spots for plasmon resonance sensing, each of said assay spots comprising a discrete metallic island, a said metallic island comprising a plurality of metallic nanoparticles to which are attached functionalizing molecules for binding to a said biological target, different said islands bearing different said functionalizing molecules for binding to different ones of said biological targets, and wherein total internal reflection of light at said surface at a wavelength at or near a said plasmon resonance results in scattering of said light away from said surface, said scattering being modulated by said binding of said biological targets.

22 Claims, 11 Drawing Sheets

U.S. PATENT DOCUMENTS

| | | | |
|---|---|---|---|
| 6,242,193 B1 * | 6/2001 | Anazawa et al. | 435/6.12 |
| 7,483,140 B1 * | 1/2009 | Cho et al. | 356/445 |
| 2005/0219542 A1 * | 10/2005 | Adams et al. | 356/445 |
| 2006/0066249 A1 | 3/2006 | Wark et al. | |
| 2007/0166763 A1 * | 7/2007 | Ho et al. | 435/7.1 |

OTHER PUBLICATIONS

Shumaker-Parry et al ("Parallel, Quantitative Measurement of Protein Binding to a 120-Element Double-Stranded DNA Array in Real Time Using Surface Plasmon Resonance Microscopy" Anal. Chem. 2004, pp. 2071-2082.*

Olkhov, et al., "Label-free antibody-antigen binding detection by optical sensor array based on surface-synthesized gold nanoparticle," Biosensors & Bioelectronics, Elsevier Science Publishers, Barking, GB, vol. 23, No. 8, Dec. 15, 2007, pp. 1298-1302.

Xiang, Yan-Juan, et al., "Seed-mediated growth of gold nanoparticles using self-assembled monolayer of polystyrene microspheres as nanotemplate arrays," Chinese Physics, Institute of Physics Publishing, Bristol, US, vol. 15, No. 9, Sep. 1, 2006, pp. 2080-2086.

ISR of International Application No. PCT/GB08/050202 dated Sep. 12, 2008.

* cited by examiner

PHOTONIC BIOSENSOR ARRAYS

CROSS-REFERENCE TO RELATED APPLICATIONS

This application is U.S. national phase filing under 35 U.S.C. §371 of PCT/GB2008/050202 filed Mar. 19, 2008 and claims priority from United Kingdom Application No. GB 0705594.0 which was filed on Mar. 23, 2007.

FIELD OF THE INVENTION

This invention relates to photonic biosensor arrays in particular employing plasmon resonance based sensing, and to methods and apparatus for reading such arrays.

This application relates to the co-pending UK patent application number 0705605.7 (and the corresponding PCT application filed on the same day as this application by the same applicant), the entire contents both of which are hereby incorporated by reference.

BACKGROUND TO THE INVENTION

In general a photonic biosensor array, sometimes called microarray or biochip, comprises a collection of probe spots to which different targets may attach. For example in the case of a DNA microarray the probes are oligonucleotides, cDNA or similar which are hybridised with fluorescence labelled samples, typically of two colours, one for the patient the other for the control. Fluorescence from the hybridised array is then viewed to determine to which spots binding has occurred. There are other types of array such as protein arrays (including antibody arrays) where spots of protein molecules (or antibodies) are used to identify the complementary entity (antibodies or proteins). Thus chemical compound arrays may be employed to search for proteins and other biologically active molecules again by employing functionalising molecules or entities in an array of spots which bind with specific biological targets. In general, however, all these techniques employ fluorescence labelling of the targets to detect binding events on the array.

By contrast the techniques we describe here do not employ fluorescence but instead rely upon plasmon resonance-based sensing. Broadly speaking in this technique total internal reflection of light is used to generate an evanescent wave which excites plasmons (a collective electronic excitation) in a metallic conductor, which are modified by the presence of a target molecule on the surface of the conductor. The modification results in a shift, generally in both wavelength and amplitude, of the plasmon resonance peak detectable in the totally internally reflected light. Plasmon resonance-based sensing has the ability to detect very small changes in the effective refractive index in a medium adjacent the surface of the metallic conductor, for example down to $\Delta n$ of the order of $10^{-4}$ refractive index units (RIU).

It is known to employ label-free surface plasmon resonance (SPR) based technology for studying biomolecular interaction in real time and, in particular, technology for this is available from the Swedish company BIAcore AB; for background technical information see published BIAcore patent applications such as WO 2006/135309, WO 94/00751, U.S. Pat. No. 4,997,278, and WO 97/19375. However BIAcore employ a continuous metal surface. Some further technical background information relating to plasmon resonance-based sensing in a different context (evanescent wave cavity ringdown spectroscopy) can be found in Evanes Co patent application WO 2005/088277.

There is, however, a need to provide improved microarray assay techniques, in particular with increased sensitivity. The applicants have recognised that, in principle, refractive index changes of orders of magnitude better than $10^{-4}$ RIU are potentially possible. Such increased sensitivity could provide a doctor with a great deal of information for help in diagnosing a pathological condition, especially if techniques could be found to address the non-specific binding events which could swamp any genuine signal at high sensitivities. Embodiments of the techniques we describe provide a step towards solutions of these problems.

SUMMARY OF THE INVENTION

According to a first aspect of the invention there is therefore provided a biosensor array for plasmon resonance-based sensing of a plurality of different biological targets simultaneously, the array comprising a transparent substrate having a surface bearing a plurality of assay spots for plasmon resonance sensing, each of said assay spots comprising a discrete metallic island, a said metallic island comprising a plurality of metallic nanoparticles to which are attached functionalising molecules for binding to a said biological target, different said islands bearing different said functionalising molecules for binding to different ones of said biological targets, and wherein total internal reflection of light at said surface at a wavelength at or near a said plasmon resonance results in scattering of said light away from said surface, said scattering being modulated by said binding of said biological targets.

In some preferred embodiments the metallic nanoparticles, which are preferably of gold, have at least one dimension of less than 30 nm, preferably less than about 25 nm. At this point the interaction between the evanescent wave and the metal changes from being dominated by absorption to being dominated by scattering. In some preferred embodiments the nanoparticles form optical antennas, that is, in embodiments, pairs of rod-like nanoparticles separated by a gap of similar dimensions to the width of a rod. More generally such an optical antenna may comprise an adjacent pair of nanoparticles, preferably each with a length:width aspect ratio of greater than 2:1, and preferably having adjacent ends separated by a gap of less than 100 nm, preferably less than 50 nm. In some preferred embodiments these comprise rod-shaped nanoparticles but other shaped nanoparticles may also be employed, for example generally triangular nanoparticles, or a combination of different shaped nanoparticles such as a rod-shaped and an adjacent generally triangular nanoparticle.

In particular, preferably each nanoparticle of an adjacent pair of nanoparticles has a length which is resonant for a plasmon wavelength in the metal, more particularly having a length which is approximately equal to an odd integral number of a plasmon half-wavelengths. The plasmon wavelength can be determined from the complex refractive index of the metal (for example 0.188+5.39i for the complex refractive index of gold) and from the wavelength of the illuminating light; preferably each nanoparticle of the pair of nanoparticles has a plasmon resonant length corresponding to an illuminating light wavelength of between 150 nm 1500 nm, more preferably 250 nm to 1000 nm, most preferably 450 nm to 900 nm (for 1 and/or 3 plasmon half-wavelengths). Preferably each of the adjacent pair of nanoparticles have substantially the same resonant length.

The inventors believe that the enhanced electric field in the gap between the nanoparticles also enhances Raleigh scattering, and hence the overall sensitivity of the technique. More generally, employing discrete islands of nanoparticles rather than a continuous surface in a biophotonic array as described above facilitates use of the array for detection of a plurality of different biological targets simultaneously.

Unlike conventional microarrays, embodiments of the above-described array allow the same chemistry to be employed to attach a plurality of different types of functionalising molecule to the metallic nanoparticles of the different islands. Thus whereas conventionally each different fluorescent label requires a separate chemical process to attach the label to a target or potential target, an array of the type we describe is suitable for use with an automated fabrication method.

Thus in a further aspect the invention provides a method of fabricating a biosensor array for plasmon resonance-based sensing of a plurality of different biological targets, the array comprising a transparent substrate having a surface bearing a plurality of assay spots for plasmon resonance sensing, each of said assay spots comprising a discrete metallic island to which is attached functionalising molecules for binding to a said biological target, different said islands bearing different said functionalising molecules for binding to different ones of said biological targets, and wherein total internal reflection of light at said surface at a wavelength at or near a said plasmon resonance results in scattering of said light away from said surface, said scattering being modulated by said binding of said biological targets, the method comprising: forming an array of said metallic islands on a transparent substrate; and functionalising each said island with a different functionalising molecule using a common chemical process to attach said different functionalising molecules to said metallic islands.

More particularly in preferred embodiments the functionalising of the metallic islands uses a solution deposition head such as inkjet print head under automatic control to collect a plurality of functionalising molecules from a corresponding plurality of reservoirs, and to deposit these onto a respective plurality of the metallic islands. In this way an array may be provided with a very large number of different functionalising molecules without the need for special chemistry to attach each one.

As the skilled person will understand, many different types of functionalising molecule may be employed including, but not limited to: oligonucleotides, cDNA, RNA such as mRNA, proteins, antibodies, antigens, and in general anything which binds to a specific biological target molecule (including potential drug molecules).

The same ligand may be used to attach many different functionalising molecules to the metallic nanoparticles. Suitable ligands include, but are not limited to, DSP (dithiobis succinimidyl propionate) and related materials, a streptavidin-biotin link may additionally or alternatively be employed.

In some preferred embodiments the array includes a plurality of control spots, in particular spots lacking any such functionalising molecules. Preferably these are physically close to the functionalised assay spots, for example less than 200 µm or 100 µm, or 50 µm. Preferably each functionalised spot has an associated control spot. This is important in a very high sensitivity array of the type we describe since the temperature coefficient for refractive index variations can be of order $10^{-3}$ to $10^{-4}/°$ C. and thus even temperature changes of $\frac{1}{1000}°$ C. can have a significant effect on the results. Similarly spatial and temporal variations in the illumination of the array can also have a significant impact on the measured output. In practice without the use of control spots the signal from the array can merely appear to be noise.

In some preferred embodiments a control spot comprises an array of metallic elements which is configured to produce an interference or fringe pattern when the control spot is viewed. More particularly when such a control spot is imaged the imaging device will "see" a number of fringes the spacing of which is dependent on the sensed medium and it has been observed that bulk properties of the medium, in particular bulk refractive index, dominate the effects on the appearance of the fringes. Thus it has been determined experimentally that the separation of the fringes may be employed as measure (relative or absolute) of the bulk refractive index of the sensed medium. Preferably such a control spot is viewed substantially normal to the surface of the array. A control spot of this type enables a degree of compensation to be applied for a variable degree of non-specific binding which may be present, for example, due to a varying protein load in the sensed medium.

In preferred embodiments the substrate includes means for coupling light into the array. Thus in some embodiments the array may be fabricated on a substrate which is configured as a Dove prism. However in some other preferred embodiments light is launched into the edge of a substantially flat, planar substrate which waveguides the light within the thickness of the substrate; such an edge coupling may comprise, for example, a lens on the edge of the substrate or a grating on a surface of the substrate. A waveguided configuration can substantially reduce the cost of the optical components in a practical embodiment of reading apparatus for the array.

A side-coupled configuration has been found to be particularly convenient for a disposable configuration of the biosensor array, for example for use outside a laboratory or hospital environment, say in a doctor's surgery. For such a disposable configuration low cost and ease of interfacing and of use are important and it has been found that with a side-coupled configuration one or two laser diodes or LEDs may be mounted on one or more sides of the display so that an electrical rather than an optical connection can be made to the device. Further it has been found that complex and costly fluidics may be omitted for determining greater than flow limited response kinetics—a sample may simply be deposited over the array, optionally with a cover being placed on top.

Thus in a further aspect the invention provides a disposable biosensor array component for plasmon resonance-based sensing apparatus, the component comprising a substrate bearing a plurality of plasmon resonance sensing assay spots, and wherein said substrate further includes at least one light emitting or laser diode mounted to the substrate to direct waveguided light in a lateral direction through said substrate.

In another aspect the invention provides a method of plasmon resonance-based sensing of a plurality of different biological targets simultaneously, the method comprising: coupling light of at least one wavelength into a biosensor array such that total internal reflection of said light at said surface generates an evanescent wave field which excites plasmons in said functionalised metallic nanoparticles and scatters said light; flowing a fluid carrying a plurality of said biological targets for analysis over said array; imaging said scattered light from said array to generate image data for said biological targets carried by said fluid; and analysing said image data to determine levels of said biological targets carried by said fluid.

Thus, in embodiments, we employ a particularly advantageous technique, which interrogates dark-field scattering from the array rather than analysis of the totally internally reflected light. In some preferred embodiments, therefore, the array is viewed from below, for example through a Dove prism optically coupled to the array. (This technique may be employed when imaging a surface plasmon-based biosensor array, and is not restricted to the particular types of surface plasmon-based arrays described above).

In some preferred embodiments the imaging is performed in real time to follow the binding kinetics of the targets. This can generate a time series of data values for each spot, hence facilitating identifying a potential pathological condition by matching binding kinetics additionally or alternatively to a bound level of the target per se. Thus a more accurate "fingerprint" of a condition may be established.

In some preferred embodiments light of two wavelengths is employed, one to either side of a plasmon resonance peak. The signals at these two different wavelengths may then be combined for increased accuracy/sensitivity, in particular by forming a ratio of the signals (intensity changes) at the two different wavelengths. More particularly if the wavelengths straddle the peak then if the peak moves in wavelengths then one signal may go up whilst the other goes down so that forming a ratio (or combining by subtracting) will enhance the combined signal.

The scattering from the array may be viewed from a front side (i.e. the surface carrying the spots) or from a back side (i.e. through the thickness of the substrate towards the spots). Viewing from the back side has the advantage of freeing the top surface for biology without interfering with the optical path. In both cases, however, dark-field scattering is present.

The peak of the surface plasmon resonance is also dependent upon the incident angle of the totally internally reflecting light. A binding interaction may change the effective angular maximum and hence, if the reading angle (total internal reflectance angle) is fixed, this may also effectively shift peak resulting in a detection signal. In embodiments polarised light may be employed since in general different plasmon resonance signals are expected for s and p polarised light. Thus the reader may also determine separate detection signals at one or more wavelengths for two different polarisations, in particular s and p polarisations. These polarisation-dependent components may be combined, again by ratioing and/or subtraction to form a differential signal (or in the case of dual wavelength illumination a further differential signal), again to enhance discrimination and/or sensitivity.

Preferably the analysing compares a signal from one spot with a signal from another of the spots to compensate for non-specific binding interactions. The (one or more) spots for comparison may either be a functionalised spot or a control spot, as described above. It has been found that by subtracting the signal from different, physically closely spaced spots noise which would otherwise dominate the signal can be effectively removed.

Embodiments of the method may thus determine a differential binding signal. To see how this works in the case of a functionalised spot, consider the case of an array which has spots of bovine serum albumin, (BSA) and fibrinogen; blood serum may have an antibody to BSA, aBSA but if the animal (or human) from which the blood was obtained needs fibrinogen then no antibody to fibrinogen should be present. Thus binding events will include non-specific binding events for fibrinogen and a combination of non-specific and specific binding events for BSA. Thus it can be seen that in, say, an antibody array some spots may include polyclonal as well as monoclonal antibodies.

Unexpectedly it has been found that compensating signals as described above allow extremely sensitive detection of specific binding events against a high level background of non-specific binding events.

The invention further provides apparatus comprising means to implement the above-described methods and processor control code to control apparatus to implement the above-described methods, in particular on a data carrier such as a disk, CD- or DVD-ROM, programmed memory such as read-only memory (Firmware), or on a data carrier such as an optical or electrical signal carrier. Code (and/or data) to implement embodiments of the invention may comprise source, object or executable code in a conventional programming language (interpreted or compiled) such as C, or assembly code. As the skilled person will appreciate such code and/or data may be distributed between a plurality of coupled components in communication with one another.

In a complementary aspect the invention provides apparatus for plasmon resonance-based sensing of a plurality of different biological targets, the apparatus comprising: means for coupling light of at least one wavelength into a biosensor array such that total internal reflection of said light at said surface generates an evanescent wave field which excites plasmons in said functionalised metallic nanoparticles and scatters said light; means for flowing a fluid carrying a plurality of said biological targets for analysis over said array; means for imaging said scattered light from said array to generate image data for said biological targets carried by said fluid; and means for analysing said image data to determine levels of said biological targets carried by said fluid.

In a related aspect the invention further provides apparatus for reading a plasmon resonance sensing array for plasmon resonance-based sensing of a plurality of different biological targets, the array comprising a transparent substrate having a surface bearing a plurality of assay spots for plasmon resonance sensing, each of said assay spots comprising a discrete metallic island to which is attached functionalising molecules for binding to a said biological target, different said islands bearing different said functionalising molecules for binding to different ones of said biological targets, and wherein total internal reflection of light at said surface at a wavelength at or near a said plasmon resonance results in scattering of said light away from said surface, said scattering being modulated by said binding of said biological targets, the apparatus comprising: a light source to generate light at two different substantially monochromatic wavelengths; an optical coupling device to couple light from said light source into said sensing array; an imaging system to image light from said array at said two different wavelengths scattered by plasmon resonance in said metallic islands, and to generate image data; and an image analysis system coupled to said imaging system to receive said image data and to analyse said plasmon-resonance scattered light to determine levels of said different biological targets attached to said array.

It is difficult to perform sensitive surface plasmon ellipsometry on an array of assay spots.

The invention also therefore provides apparatus for reading a plasmon resonance sensing array for plasmon resonance-based sensing of a plurality of different biological targets, the array comprising a transparent substrate having a surface bearing a plurality of assay spots for plasmon resonance sensing, each of said assay spots comprising a discrete metallic island to which are attached functionalising molecules for binding to a said biological target, different said islands bearing different said functionalising molecules for binding to different ones of said biological targets, the apparatus comprising: a light source to generate polarised light; a polarisation modulator to modulate a polarisation of said polarised light; an optical system to illuminate said array with said modulated polarised light to generate plasmons in said assay spots by total internal reflection of said polarised light; and a detection system to detect an orientation of an elliptical polarisation of said totally internally reflected modulated polarised light; and an output to output a target sensing signal dependent on binding of a said biological target to a said functionalising molecule responsive to detection of a change in said elliptical polarisation orientation.

Preferably the polarisation modulator is pixellated for separate interrogation of the assay spots, and the detection system may then be configured to enable separation of the signals from different assay spots.

Embodiments of this pixellated fast optical phase differential surface plasmon technique ameliorate requirements on the camera performance: Vertically (TM) polarized light may excite a surface plasmon resonance at a metal/dielectric interface in the Kretschmann configuration. There is a significant phase change of the reflected TM polarized light as the SP resonance is traversed, whether by changing the incident angle, the wavelength of the light or the refractive index of the bounding dielectric. If linearly polarized light consisting of both TM and TE polarizations is incident upon the SP system, then the TM polarized component undergoes a phase change, whereas the TE polarized component does not. The result of having two orthogonal components phase shifted with respect to each other is that the light reflected from the SP system becomes elliptically polarized. Because the phase changes rapidly as the SPR is traversed, the ellipticity and orientation of the polarization ellipse also changes rapidly. The azimuth of the ellipse is rotated by approximately 1° for a refractive index change of only $5 \times 10^{-5}$. Therefore, all that is needed to produce a sensitive refractive index sensor is a sensitive measure of the rotation of the polarization ellipse. If the plane of polarization of incident light upon a SP system is dithered sinusoidally and the reflected signal monitored using a phase sensitive detector with the reference set at the dither frequency, then the zeros of this differential signal correspond to the azimuth or the azimuth $\pm \pi/2$ rad of the output polarization ellipse. If the refractive index of the bounding dielectric medium is altered, the angular position of the zero in the differential signal also changes. Recently, we have demonstrated this same effect using a chiral hybrid aligned Liquid Crystal (LC) cell, which is low voltage driven, has low power consumption and is cheap, small, and lightweight. Further, it also allows simple pixellisation, for imaging or sampling many areas simultaneously. The use of a chiral dopant in the HAN cell means that there is a twist in the director, which produces a rotation in the plane of polarization of transmitted light through the cell. Then when a voltage is applied across the cell the liquid crystal director re-orientates and untwists to an extent dictated by the voltage (without a threshold as it is a HAN cell). Therefore, the degree of polarization rotation is controlled by the applied voltage. This complete arrangement has been tested and has a sensitivity to changes in index of $2 \times 10^{-7}$, this corresponds to a polarization rotation resolution of only 0.02°. Improvements in the optical configuration, allowing brighter signals and also detector electronics should increase the angular sensitivity by two orders of magnitude.

In a further complementary aspect the invention provides a method of plasmon resonance-based sensing of a plurality of different biological targets simultaneously, the method comprising: coupling light of at least one wavelength into a biosensor array as describe above such that total internal reflection of said light at said surface generates an evanescent wave field which excites plasmons in said functionalised metallic nanoparticles, said light comprising polarised light with polarisation modulation; detecting an orientation of an elliptical polarisation of said totally internally reflected modulated polarised light; and outputting a target sensing signal dependent on binding of a said biological target to a said functionalising molecule responsive to detection of a change in said elliptical polarisation orientation.

In this specification nanoparticles refers to particles with at least one dimension, preferably two or three dimensions, of less than 1 µm, preferably 500 nm, more preferably 300 nm. Embodiments may have all dimensions less than 1 µm and at least one dimension less than 100 nm.

In a further aspect the invention provides a biosensor array for plasmon resonance-based sensing, the array having a surface bearing a plurality of assay spots, each of said assay spots comprising a conducting material for plasmon resonance sensing, and wherein the array further comprises at least one control spot, the control spot bearing a pattern of conductive elements. The pattern of conductive elements is configured such that light emitted by plasmon resonance (from plasmons excited in the conductive elements) in the control spot exhibits a pattern of interference or fringes when viewed or imaged, for example along a direction substantially normal to the surface of the array.

The control spot may therefore comprise an array of the conductive elements, in particular a substantially regular array. A pitch of the array of conductive elements may be of order of the wavelength of illuminating and/or emitted light and may therefore be in the range 100 nm-2000 nm, more particularly in the range 300 nm-1400 nm. The control spot may have a maximum overall size in the plane of the array of greater than 1 µm or greater than 10 µm, for example in the range 10 µm to 500 µm. In embodiments each of the conductive elements preferably has a maximum dimension smaller than a wavelength of the illuminating/emitted light, for example smaller than 100 nm. Preferably then the elements are spaced apart by a distance of greater than this maximum dimension. In embodiments a conductive element may have an aspect ratio of greater 1.5:1 or greater than 2:1 and may, for example, have a generally rod-shaped or triangular appearance. Conveniently the conductive elements may be formed within a layer of metal, such as gold, on the surface of the biosensor.

In a related aspect the invention provides a method of measuring or controlling for variation in bulk refractive index of a fluid the composition of which is sensed by a plasmon resonance-based sensor, the method comprising: providing a control region on said plasmon resonance-based sensor, said control region comprising a pattern of conductive elements; detecting a fringe or interference pattern in light emitted by said pattern of conductive elements; and using said fringe or interference pattern to measure or control for said variation in said bulk refractive index of said sensed fluid.

The control region may be employed to determine a change in bulk refractive index of the sensed fluid rather than, say, an absolute value of the bulk refractive index; alternatively the sensor may be calibrated using fluids of the type of interest (for example, blood) whose bulk refractive index has been measured by other techniques.

The invention further provides a method of determining a binding rate constant of a target in a fluid using a plasmon resonance-based biosensor array, the array including at least one assay spot and at least one control spot. The method comprises determining a binding rate of the target to one of the assay spots (functionalised to detect the target), and then compensating the determined binding rate for non-specific binding, for example by other materials such as proteins, by measuring or controlling for variation in a bulk refractive index of the sensed fluid using a control spot, in particular as described above.

Features of the above-described embodiments and aspects of the invention may be combined in any permutation.

BRIEF DESCRIPTION OF THE DRAWINGS

These and other aspects of the invention will now be further described, by way of example only, with reference to the accompanying figures in which.

DETAILED DESCRIPTION OF PREFERRED EMBODIMENTS

Figure 1:
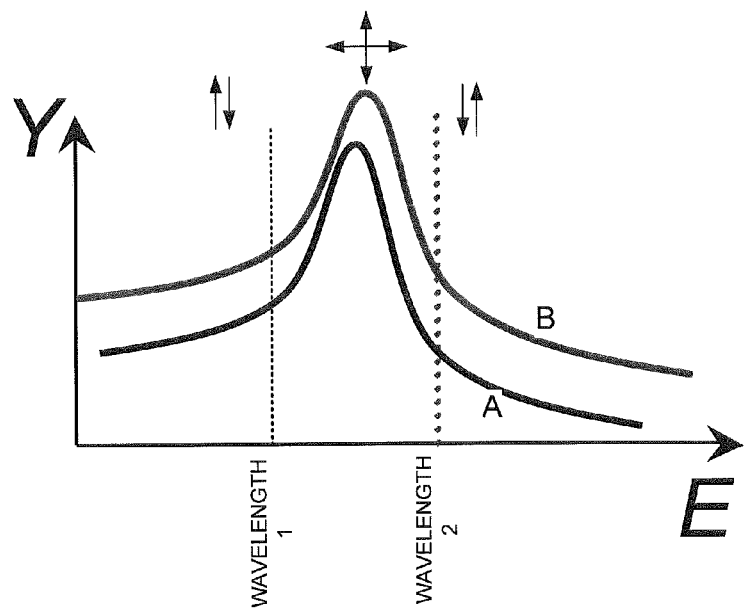
FIG. 1 shows, schematically, a change of scattering cross-section through to a change in plasmon resonance.

Referring first to FIG. 1, this illustrates, schematically, a graph of scattered light intensity (Y) against wavelength illustrating, in this example, an increase in scattering cross-section from curve A to curve B which results in an increase in the signal at wavelengths 1 and 2. It will be appreciated that a shift in the plasmon resonance will tent to result in an increase in the signal at one wavelength and a decrease in the signal at the other, if the two wavelengths straddle the peak. An effective change in the angular response of the plasmon resonance, for example caused by a binding event, will for a fixed angle of incidence cause a shift in the intensity and/or position of the resonance. The sensitivity to refractive index variations can be calibrated by, for example, using test solutions of water and isopropanol.

Figure 2A:
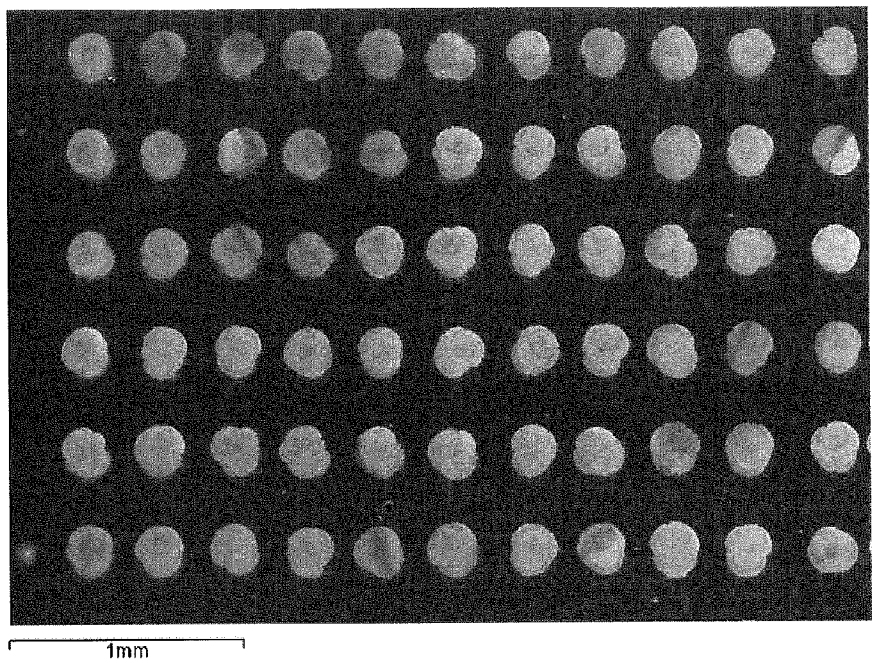
FIGS. 2a to 2e show, respectively, a photograph of an embodiment of a photonic biosensor array according to an embodiment of the invention, nanoparticles on a metallic island of the array of FIG. 2a, an enlarged image of the nanoparticles of FIG. 2b, a schematic diagram of a nanoparticle optical antenna, and a schematic illustration of all alternative configurations of a nanoparticle optical antenna.
Figure 2B:
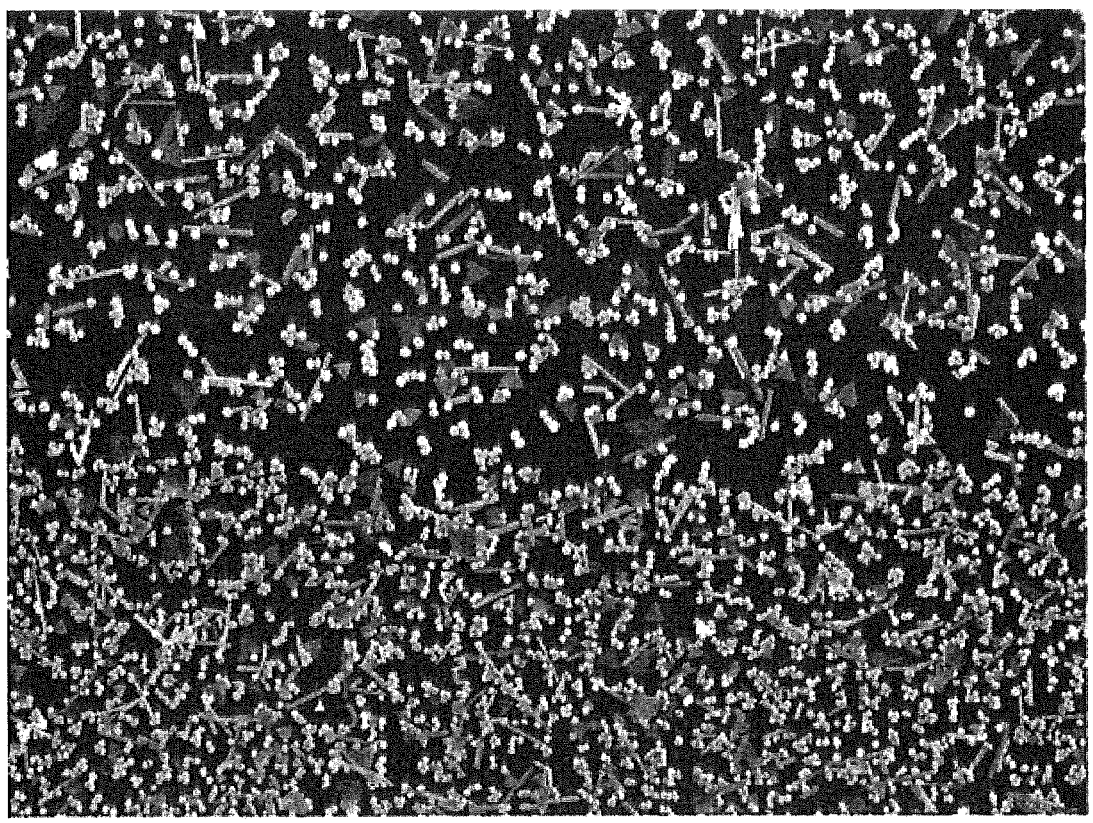
Figure 2C:
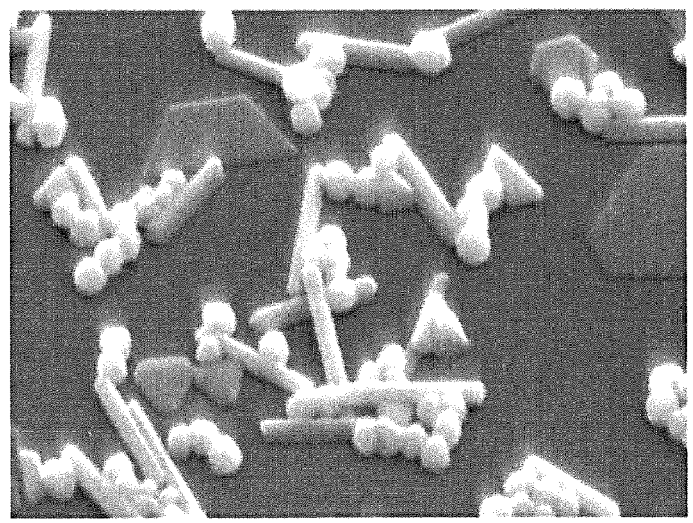

FIGS. 2a to 2c show a plasmon resonance-based sensing biosensor array at increasing levels of magnification. In FIG. 2c, in particular, it can be seen that rod-like triangular and pancake-shaped (gold) nanoparticles are present. This has advantages as explained further below. Broadly speaking a surface of the type illustrated in FIG. 2c can be fabricated by depositing small seed nanoparticles and then growing larger "crystals" in an environment in which local growth is effectively sterically hindered, for example by a surfactant such as CTAB.

An example procedure for seed-mediated growth of gold nanoparticles on silica or glass surface is as follows:

1. 3-4 nm spherical seeds are produced by reduction of $Au^{3+}$ ($3\times10^{-4}$M $HAuCl_4$) by excess of $NaBH_4$ ($3\times10^{-3}$ M) in the presence of tri-sodium citrate capping agent ($3\times10^{-4}$M).
2. Seed particle colloid is printed in array of spots on the uncoated silica or glass surface and the slides are allowed to dry. The printed seed density (in terms of number of particles per unit of surface area) determines the density of the grown particles, therefore one can easily achieve practically any desired surface coverage (which can, of course be varied from spot to spot to produce kind of monochrome image).
3. The seeded slides are washed in water to remove excess of citrate and any particles which were not adhered to the surface.
4. The seeded slides are developed in grown solution containing $2\times10^{-4}$M $HauCl_4$, 0.1M cetyltrimethylammonium bromide (CTAB) as capping agent, and $4\times10^{-4}$M ascorbic acid as reducing agent for 20-30 minutes at 25° C. producing the variety of gold nano-shapes (shown in FIG. 2c). (In the presence of $1\times10^{-5}$M $Ag^+$ the size distribution of grown particles is more uniform and gold nanocrystals are highly faceted, which can improve sensitivity to the change of the medium refractive index).

Conditions such as temperature and reagent concentration may be varied to vary the growth pattern.

Figure 2D:
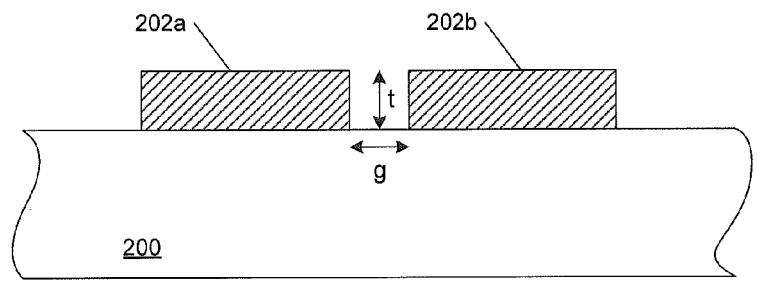
Figure 2E:
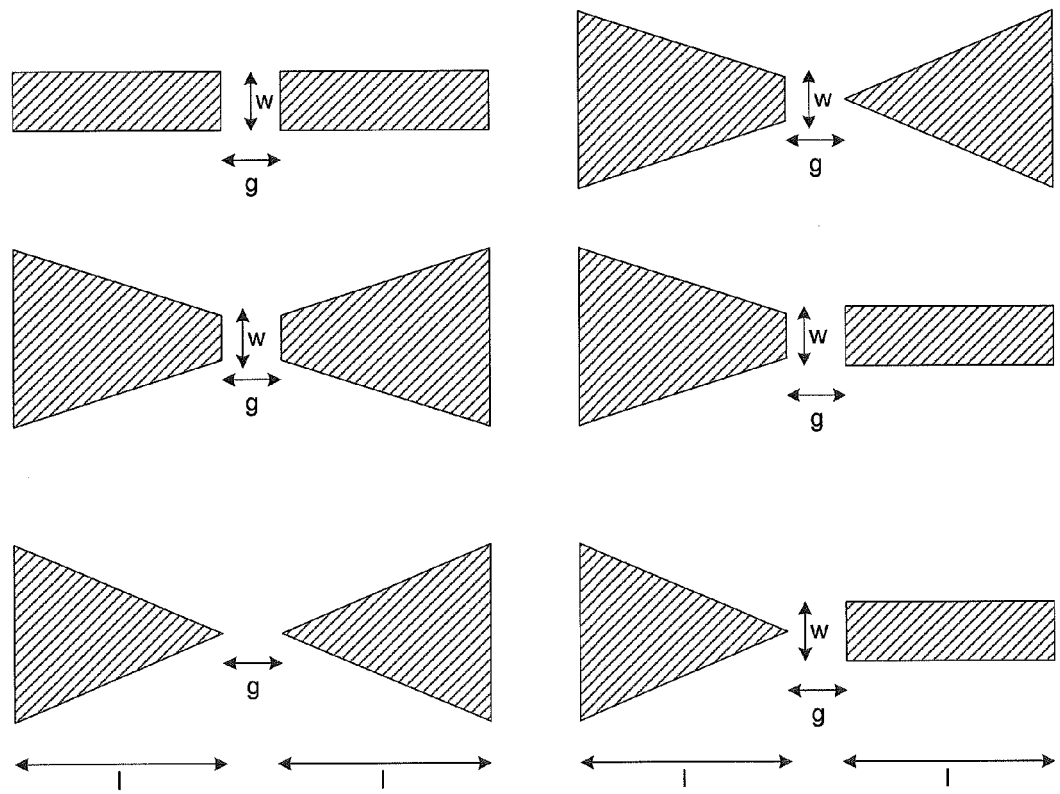

Referring now to FIG. 2d, this shows as pair of rod-like nanoparticles 202a, b on a transparent substrate 200 in vertical cross-section. FIG. 2e shows a view from above showing various alternative configurations for the nanoparticles 202. In some embodiments the length of a nanoparticle, l, may be approximately 130 nm, (a half plasmon wavelength at light wavelength of 830 nm); the dimensions w and t may be in the range 20 nm to 60 nm, for example around 30-50 nm. The gap g between the nanoparticles may be in the region 20 nm to 60 nm, for example around 30 nm. This configuration is believed to substantially enhance the electric field in the gap and hence enhance scattering mediated by plasmon resonance within the nanoparticles, thus increasing the sensitivity of the array.

Background information relating to optical antennas can be found in "Plasmonic laser antenna", E. Cubukcu, E. A. Kort, B. Crozier and F. Capasso; Applied Physics Letters 89, 093120 (2006); and "Field enhancement and gap-dependent resonance in a system of two opposing tip-to-tip Au nanotriangles", A. Sundaramurthy, K. B. Crozier, G. S. Kino, D. P. Fromm, P. J. Schuck, and W. E. Moerner, Physical Review B 72, 165409 (2005).

Alternatively e-beam or focused ion beam lithography may be employed to pattern a metal, for example gold, surface. Patterns may include an array of metallic posts or holes (creating 'hot spots' at the gaps between these).

Figures 3A, 3B, 3C:
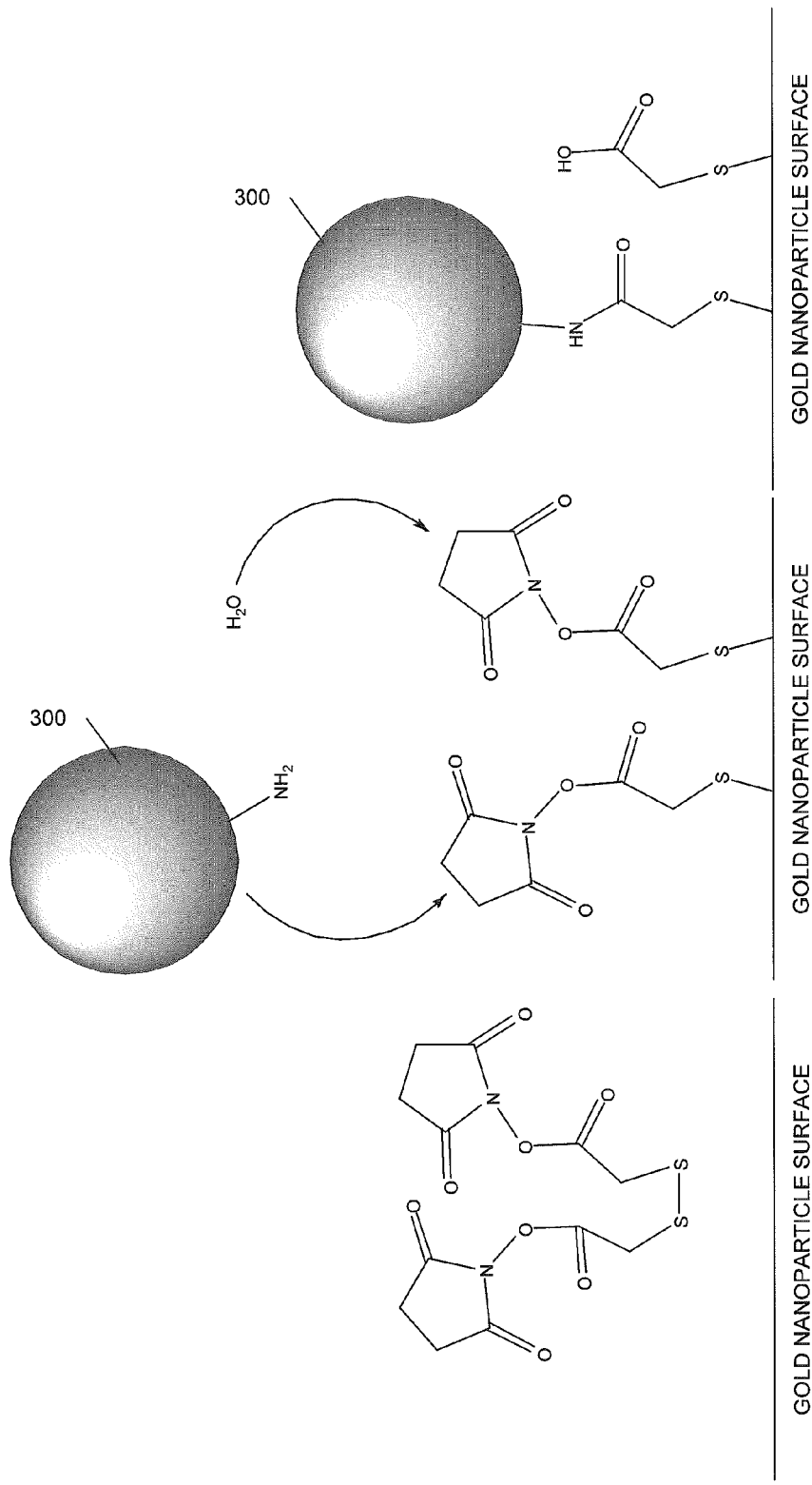
FIGS. 3a to 3c show, respectively, stages in attaching a functionalising molecule to a gold nanoparticle surface.

Having fabricated the nanoparticle islands of the spots for the microarray the nanoparticles are functionalised by attaching biomolecules of any desired type. One preferred procedure using DSP as a linkage is shown in FIGS. 3a to 3c in which a functionalising molecule 300 is shown being attached to a gold nanoparticle surface. The skilled person will understand that other techniques may also be employed for example using a streptavidin-biotin linkage. An array may be benchmarked by monitoring hybridisation of DNA sequences (the ability to monitor shorter lengths denoting better performance).

Figure 4A:
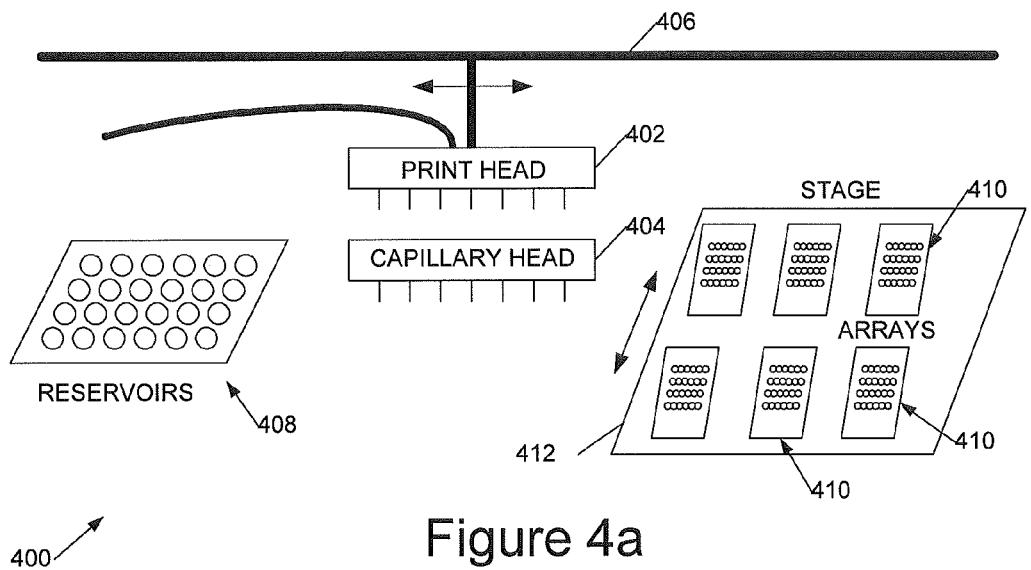
FIGS. 4a to 4c show, respectively, microarray fabrication apparatus for fabricating a microarray according to an embodiment of the invention, and first and second control spot configurations.

FIG. 4a shows apparatus 400 for automatically fabricating a plasmon sensing-based biosensor array according to an embodiment of the invention. In embodiments apparatus 400 comprises an Arrayjet Limited (Edinburgh, UK) Aj 100 instrument which has an inkjet type print head 402 coupleable to a capillary head 404 and movable on a support 406 in one dimension to collect material in solution from a plurality of reservoirs 408 and to deposit the material onto arrays 410 on a movable stage 412. (The control and cleaning mechanism is omitted for clarity).

In operation the apparatus 400 of FIG. 4a is used first to deposit seed gold nanoparticles onto the arrays, which are afterwards developed offline and then replaced on stage 412. Then the reservoirs are replaced with reservoirs containing different functionalising molecules which are then attached to the gold nanoparticles by a straightforward process of selecting the different functionalising molecules from reservoirs 408 and depositing these onto the assay spots on the arrays 410. By contrast with fluorescence-labelling techniques common linkage chemistry can be used for a wide range of different functionalising molecules, thus enabling automation of the functionalisation process. The inkjet print head 402 facilitates non-contact printing, thus preventing damage to the assay spots.

Figure 4B:
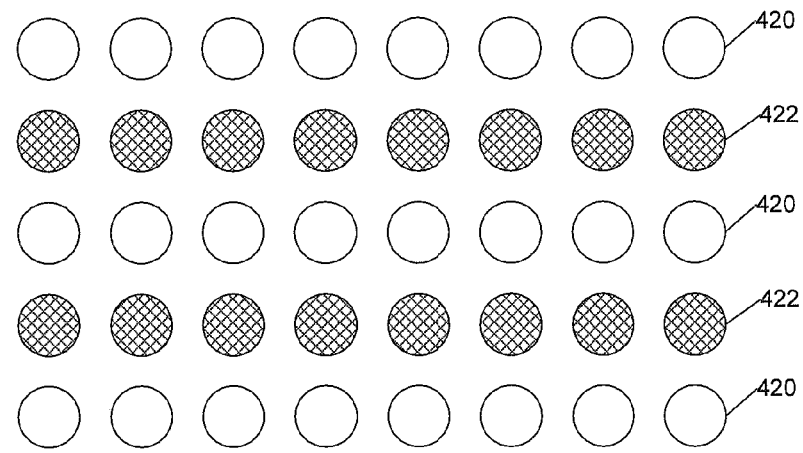
Figure 4C:
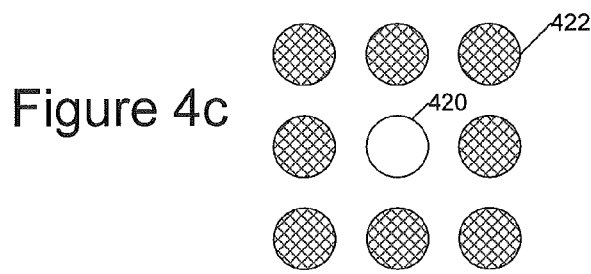

FIG. 4b shows spots on an array 410 illustrating one example configuration of assay spots 420 and associated control spots 422. FIG. 4c illustrates an alternative configuration. In practice it has been found important that the control spots are physically close to the assay spots, to enable good compensation for variations in parameters such as temperature, flow over the microarray, and illuminating light beam uniformity. Preferably at least one control spot is within 100 µm, preferably within 50 µm of an assay spot.

Figure 5A:
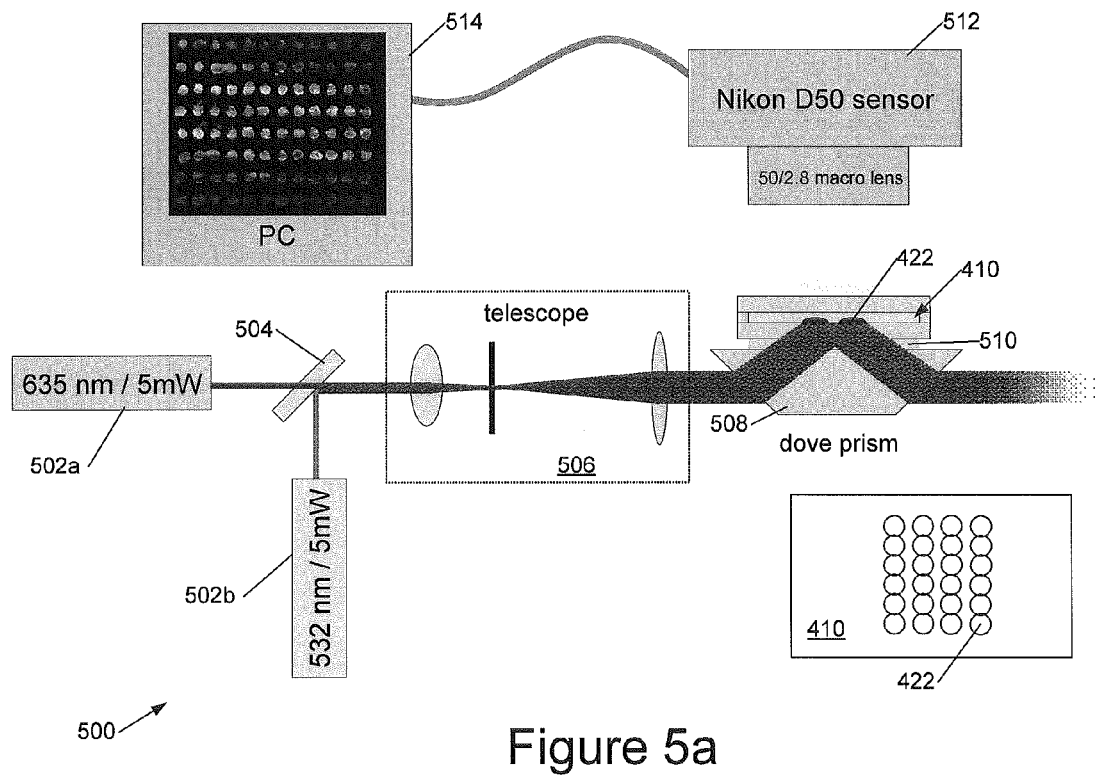
FIGS. 5a to 5c show, respectively, a plasmon biosensor array reader for dark field scattering reading of a plasmon biosensor array according to an embodiment of the invention, a schematic illustration of a waveguiding reader according to an embodiment of the invention, and a schematic illustration of a differential ellipsometric reader according to an embodiment of the invention.

FIG. 5a shows an example of scattered light reading apparatus 500 for reading assay spots using light scattered by plasmon resonance, modulated by the binding of one or more targets to one or more functionalising molecules of the array. The apparatus 500 comprises a pair of light sources 502a, b, in the illustrated example lasers although light emitting diodes may alternatively be employed. The wavelengths of these lasers are selected so as to straddle a plasmon resonance, as illustrated at 635 µm and 532 µm. The beams are combined by beam splitter 504 and provided through a telescope 506 to the microarray 410 which is placed on a totally internally reflecting surface of a Dove prism 508, coupled by index matching fluid 510. A colour digital camera 512 catches an image of the scattered light from the microarray which is provided to a computer system 514 for processing the image to identify and monitor binding kinetics of target molecules to the array. Colour camera 512 may be replaced by one, two or more monochrome cameras and, where two wavelengths are employed, wavelength selection may be performed by one or more dichroic mirrors. Preferably, but not necessarily, the imaging device has a substantially linear response to light intensity variations.

Figure 5B:
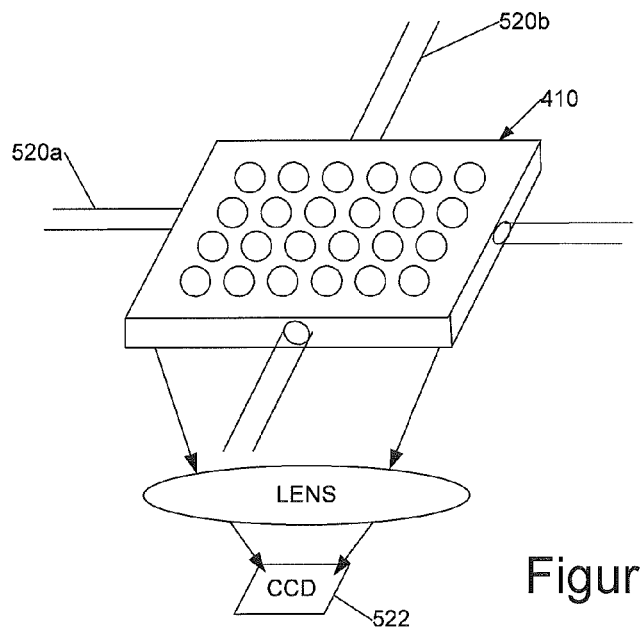

FIG. 5b shows an alternative configuration in which incident light is provided by index matched fibres 520a, b into two edges of the array 410 and waveguided within the thickness of the array. In this illustrated embodiment dark-field scattered light from the array is imaged through the back surface of the array onto a CCD (charged coupled device) or CMOS sensor 522. Preferably, as shown in FIG. 5a, light of two different wavelengths is used to illuminate the array and the sensor is configured to selectively detect each of these wavelengths, for example by filtering or by time multiplexing the illumination. Preferably, for increased sensitivity, the illuminating light is modulated and phase sensitive detection of the scattered light is employed.

In some preferred implementations of a disposable biosensor array rather than index matched fibres being used to couple light into two edges of the array, one or more laser diodes is mounted on one or more sides (edges) of the array in order to facilitate simple interfacing to apparatus for interrogating the array (by means of straightforward electrical connections to the laser diodes).

A substance to be analysed, for example blood serum, may be provided to the microarray for sensing by, for example, a syringe coupled to a duct above the assay spots to flow the substance, for example serum, over the microarray. Embodiments of the apparatus permit samples of bloody fluid to be analysed directly (optionally diluted, for example with saline) because, in embodiments the use of some spots as controls enables compensation for non-specific binding. In more sophisticated embodiments a microfluidic fan-out along one or more edges of the array of spots may be provided.

Figure 5C:
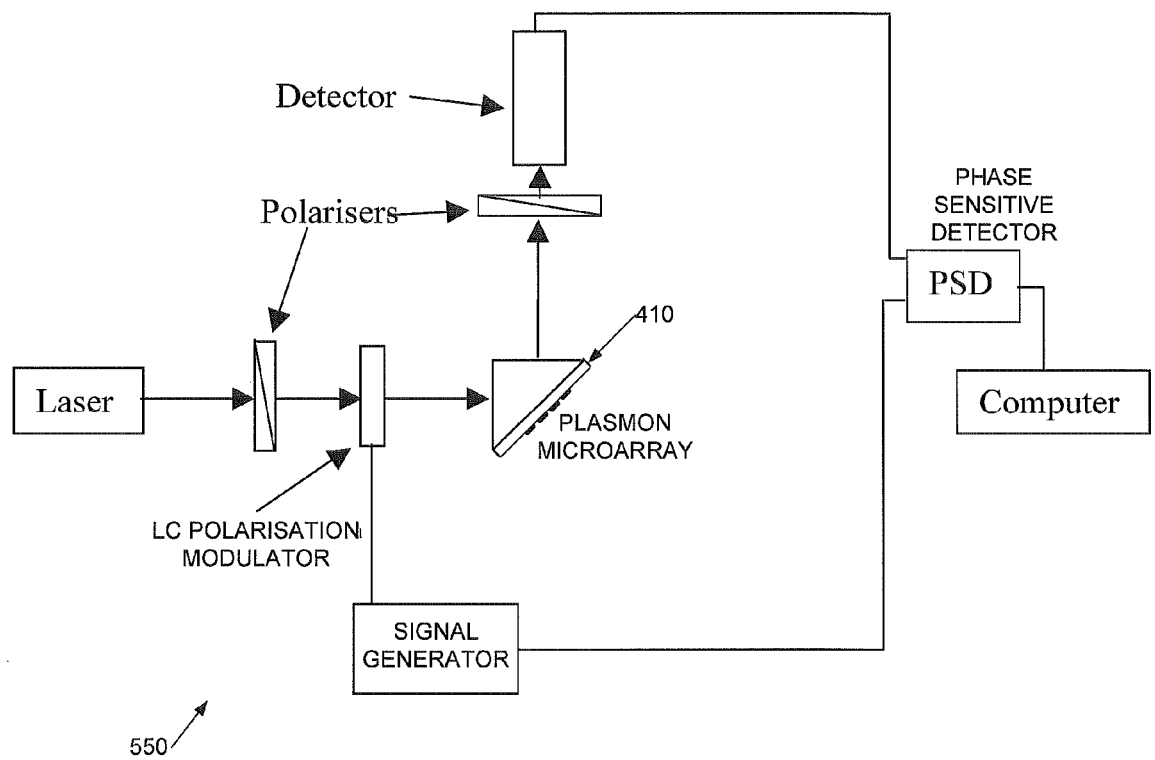
Figure 5C:
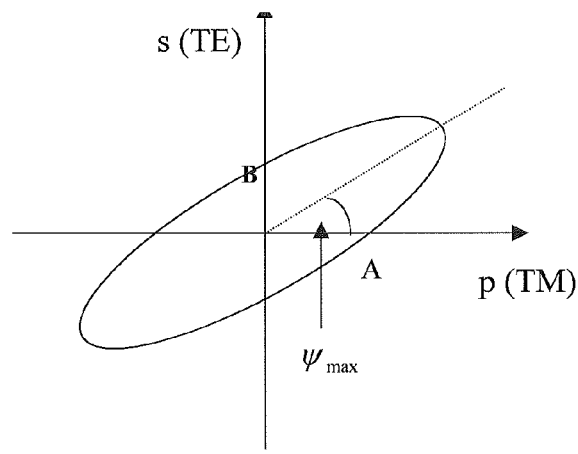

Referring now to FIG. 5c, this shows apparatus 550 which analyses the totally internally reflected light rather than the scattered light from the microarray. If linearly polarised light with both TM and TE polarisations in incident upon the plasmon resonance system, then the TM polarised component undergoes this phase change, whereas the TE polarised component does not. The result of having two orthogonal components phase shifted with respect to each other is that the light reflected from the plasmon resonance system becomes elliptically polarised. Due to the fact that the phase changes rapidly as the plasmon resonance is traversed, it follows that the ellipticity and orientation of the polarisation ellipse also changes rapidly. Only the change in the azimuth of the polarisation ellipse may be considered since the variation in this is greater, as a function of the refractive index of the bounding dielectric medium, than is the ellipticity. It can be shown through multi-layer optical modelling that the azimuth of the ellipse is rotated by approximately 1° for a refractive index change of only $5 \times 10^{-5}$ RIU. Therefore, all that is needed to produce a sensitive refractive index sensor is an accurate and sensitive way to measure the rotation of the polarisation ellipse.

If a polariser were placed in the path of the reflected beam, before a detector and rotated through an angle φ, then the signal obtained as a function of the angle of the polariser would show a cosine squared dependence. The angle at which the maximum in this dependence occurs corresponds to the azimuth of the polarisation ellipse. If the plane of polarisation of incident light upon the plasmon resonance system is dithered sinusoidally, and the signal at this dither frequency monitored, then the differential of the $\cos^2 \phi$ curve is obtained as a function of the polariser angle. The zeros of this differential signal correspond to the maxima and minima of the $\cos^2 \phi$ curve (the azimuth and the azimuth ±90°. Therefore, if the angular position of a zero is determined, the azimuth (or the azimuth ±90° is found, and, if the refractive index of the bounding dielectric medium is altered, the angular position of the zero in the differential signal also changes.

The polarisation changes caused by the incident and output faces of the prism are also taken into account in the modelling method, producing two complex amplitude coefficients: $r_p$ for the p-polarised component, and $r_s$ for the s-polarised component (which are scaled in order to incorporate the different initial intensities of the s and p-components caused by the input polariser). These two reflection coefficients of amplitude can be written in the form $$r = A\exp(i\delta_p)$$

$$r_s = B\exp(i\delta_s) \quad \text{Eqn. 1}$$

where A and B are the magnitudes of the two complex amplitude coefficients, and $\delta_p$ and $\delta_s$ are their phases relative to the incident light. The phase difference between the p and s-components is also defined as $\delta = \delta_p - \delta_s$.

If a second polariser is now placed after the prism arrangement at some angle $\psi$ (with 0° again defining the axis corresponding to purely p-polarised light) the total E-fields of the light transmitted through this polariser are given by, $$T = r_p \cos\psi + r_s \sin\psi \quad \text{Eqn. 2}$$

which, upon splitting into the real and imaginary components, gives $$T = A\cos\delta_p \cos\psi + B\cos\delta_s \sin\psi + i(A\sin\delta_p \cos\psi + B\sin\delta_s \sin\psi) \quad \text{Eqn. 3}$$

with the measured intensity being given by $$I = TT^* = A^2\cos^2\psi + B^2\sin^2\psi + 2AB\cos\psi\sin\psi\cos\delta \quad \text{Eqn. 4}$$

Since, after reflection, the two orthogonal components are no longer in phase with each other the resultant E-fields define elliptically polarised light (FIG. 5c), with the intensity for any value of $\psi$ given by Eqn. 4. If the output polariser is rotated such that the intensity is measured as a function of $\psi$, and the intensity values for $\psi=0°$ and 90° (corresponding to the values $A^2$ and $B^2$ respectively), and the angular position of the maximum of the function ($\psi_{max}$–the azimuth of the ellipse), are determined, it is possible to establish the phase between the p and s-components resulting from the excitation of the SP. This determination of the phase difference ($\delta$) is simply achieved by taking the differential of Eqn. 4 and equating it to zero; the resultant expression can then be written as $$\delta = \cos^{-1}\left(\frac{(B^2 - A^2)\tan(2\psi_{max})}{2AB}\right) \quad \text{Eqn. 5}$$

Since the s-component does not change phase upon excitation of the SP, this corresponds to the phase change of the p-component through the SP, although it is not an absolute measure of the phase since the s-component also has a non-zero phase change relative to the incident light. There are methods by which the absolute phase of the p-component through the plasmon resonance can be obtained, but as a measure for plasmon resonance sensors this complication is unnecessary, and in embodiments all that is measured is the value of $\psi_{max}$ (or $\psi_{min}$), the angles characterising the semi-major (or semi-minor axis) of the polarisation ellipse respectively. The angle $\psi_{max}$ is also known as the azimuth of the ellipse.

The phase of the p-component, and the magnitude A, change dramatically through the plasmon resonance. If the prism arrangement is oriented at a fixed angle such that the measured intensity is from the plasmon resonance edge on the high angle side of the intensity minimum, then as the refractive index of the lower medium is raised (meaning that the plasmon resonance moves to higher angles and passes through the angle being investigated) any change in $\psi_{max}$ corresponds to changes in the coefficients A and $\delta$. This produces a large variation in $\psi_{max}$ or $\psi_{min}$ for very small changes in the refractive index. It is this change in $\psi_{max}$ or $\psi_{min}$ as a function of the refractive index which can be used for plasmon resonance.

A Faraday rotator may be used to produce a dithered polarisation state. Magnetic fields were created by two concentric solenoids, one with a time-varying sinusoidal current passed through it, producing a time-varying-magnetic field and hence a time-varying rotation of the polarisation state, and one with a quasi-static current passing through it, producing a quasi-static magnetic field. This quasi-static field produces a quasi-static rotation of the polarisation state that was used to compensate for any change in the refractive index of the bounding dielectric medium by means of a feedback circuit which kept the differential signal at zero. The zero which is monitored corresponded to a minimum in the non-differential polarisation state curves since more signal is available without overloading the detector. By monitoring the current required to maintain the zero in the differential signal any change in the refractive index of the bounding dielectric medium may be observed.

Another way of producing the same effect is to use a Liquid Crystal (LC) cell, which is very cheap, small, and light weight, and also allows simple pixelisation which could lead to multiplexing of the system, allowing imaging or the sampling of many areas simultaneously. A Chiral Hybrid Aligned Nematic LC cell may be used. By adding a chiral dopant to the liquid crystal a twist of the director through the cell is produced with the amount of twist being determined by the concentration of the dopant. This twist produces a rotation in the plane of polarisation of transmitted light through the cell. If a voltage is applied across the cell the liquid crystal director re-orientates and untwists to an extent dictated by the voltage. Therefore, the amount of polarisation rotation is controlled by the applied voltage. In reality to align the LC it is necessary to apply a high frequency (>10 kHz) sine wave to the cell rather than a DC voltage to prevent electrostatic degradation of the LC (this frequency is sufficiently high that the LC can not respond to the fast oscillation, and it responds to the RMS value of the voltage). In order to produce the desired polarisation dither, an amplitude modulated (500 Hz and 300 mVp-p) high frequency carrier sine wave (50 kHz, 15Vp-p) is used. By changing the amplitude of the high frequency carrier sine wave a constant overall change in the polarisation orientation is obtained which can be used as the feedback for the system. The liquid crystal used may be ZLI-2293 (a common nematic liquid crystal) doped with CB15 (a chiral nematic liquid crystal) in proportions such that the pitch of the liquid crystal is approximately 10 microns. The cell is 5 microns thick. The method determines the azimuth of elliptically polarised light resulting from the reflection of light consisting of both s and p-components from a plasmon resonance system. In essence this is a simplified self-referenced phase determination method which has no moving parts, is relatively simple, and very sensitive. The LC cell modulation technique may also be easily pixellated for use with a sensing array as described above. More details can be found in I. R. Hooper, J. R. Sambles, "Sensing using differential surface plasmon ellipsometry", Journal of Applied Physics, Volume 96, Number 5 (September 2004), pp. 3004-3011; and in I. R. Hooper, J. R. Sambles, "Differential ellipsometric surface plasmon resonance sensors with liquid crystal polarization modulators", Applied Physics Letters, Volume 85, Number 15 (October 2004), pp. 3017-3019.

Figure 6A:
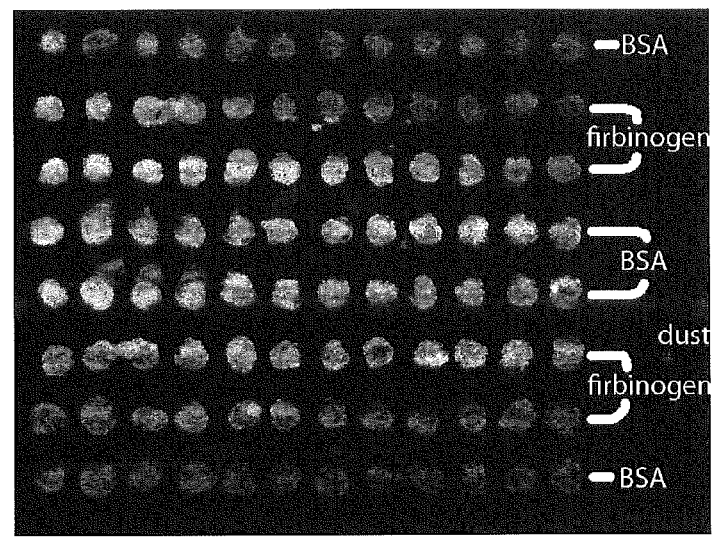
FIGS. 6a to 6c show, respectively, an image of a scattering plasmon resonance array according to an embodiment of the invention in operation, a corresponding plot of laser intensity illustrating variations in laser spot brightness over the area of the array, and example traces from the array of FIG. 6a at a single wavelength illustrating changes in scattered light intensity from two differently functionalised rows of the display with time.
Figure 6B:
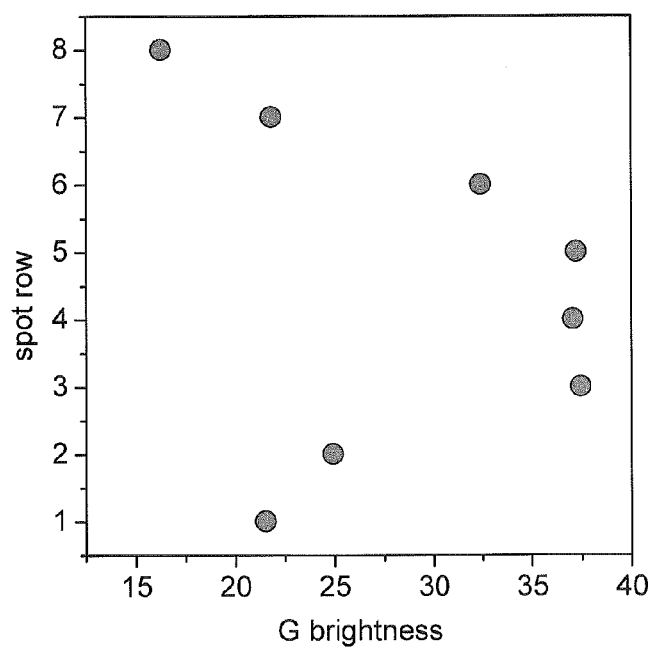

Referring now to FIG. 6a, this shows one experimentally fabricated plasmon sensing array in which fibrinogen and BSA (bovine serum albumin) were used as test functionalising molecules, sensitising the array to antibodies for each of these. As can be seen in FIG. 6a, there is a non-uniform intensity distribution over the area of the display and therefore the signals are preferably normalised using a laser intensity curve shown in FIG. 6b.

Figure 6C:
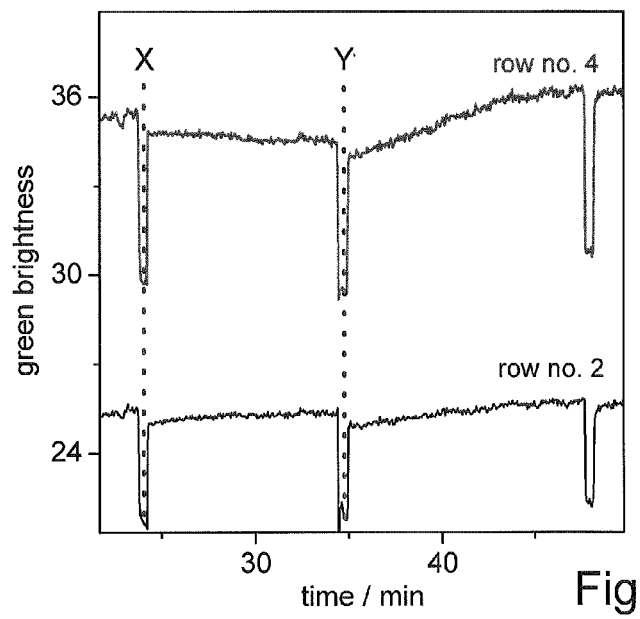

Referring to FIG. 6c, this shows curves for the green laser illumination of FIG. 5a for row 2 (fibrinogen) and row 4 (BSA), showing changes in scattering with time following infusion of the array with anti-fibrinogen (point X) and anti-albumin (point Y). The curves show some non-specific binding, and also the effect of physical washing of material from the array, but it can be seen by inspection that a ratio of the signals from the two differently sensitised assay spots or rows can be used to sensitively detect specific binding events.

Figure 7A:
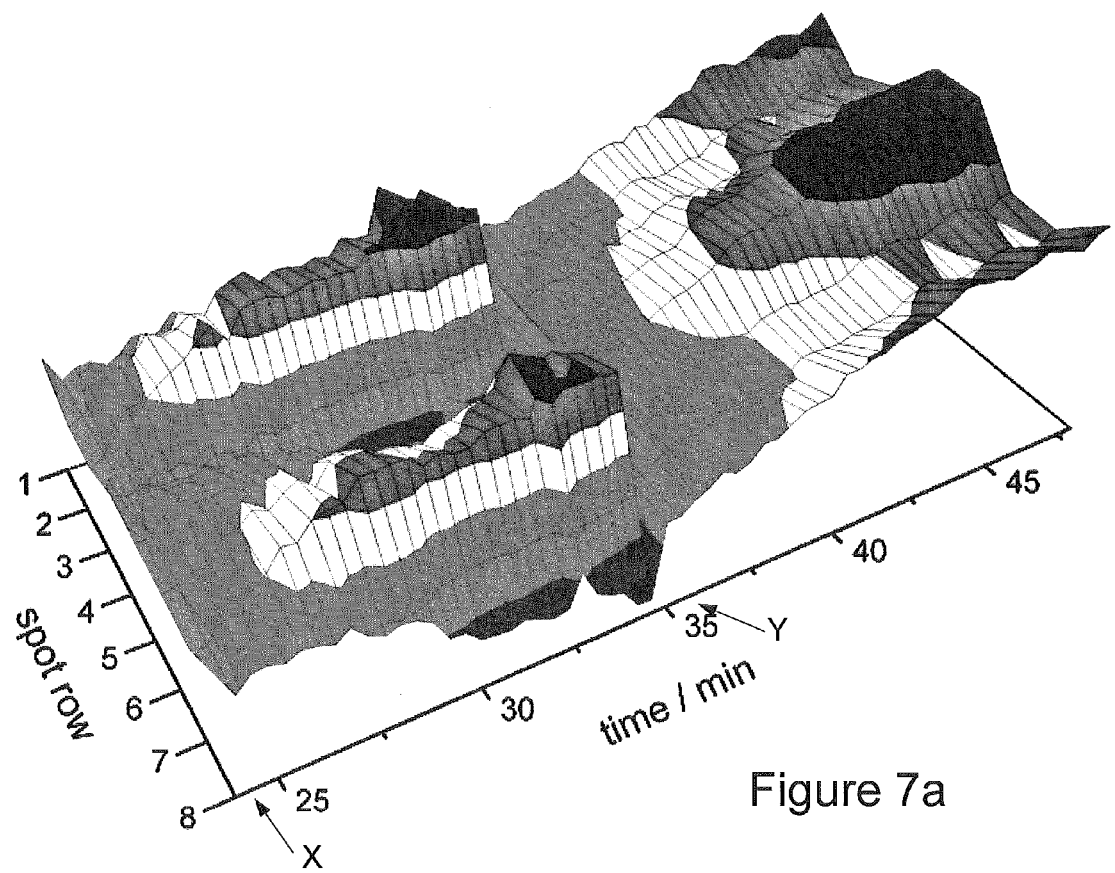
FIGS. 7a to 7c show, respectively, changes in scattered light intensity from a plurality of rows of the array over time as a three-dimensional plot and as a two-dimensional plot, and changes in scattered light intensity at a single wavelength or a single row of the array over time for two different targets and including comparison with a control.
Figure 7B:
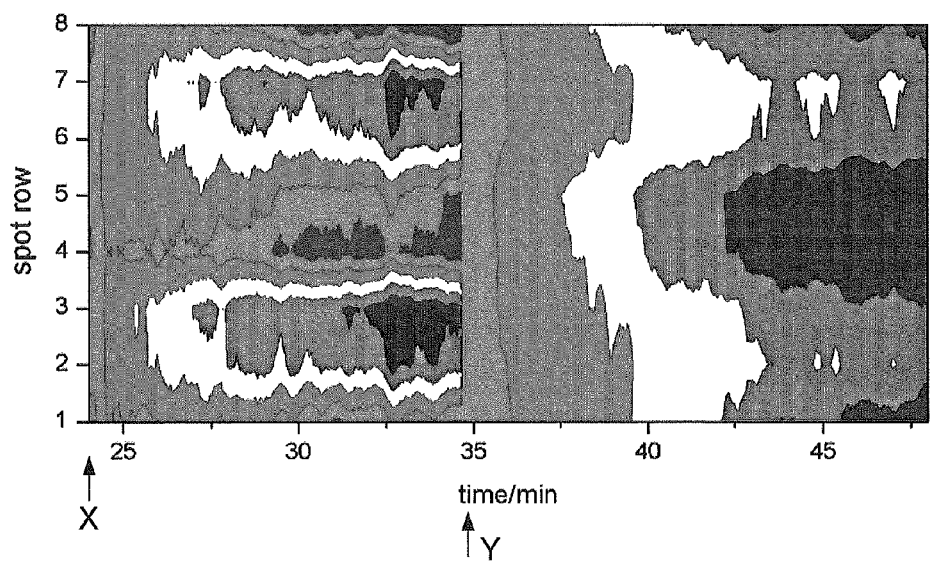
Figure 7C:
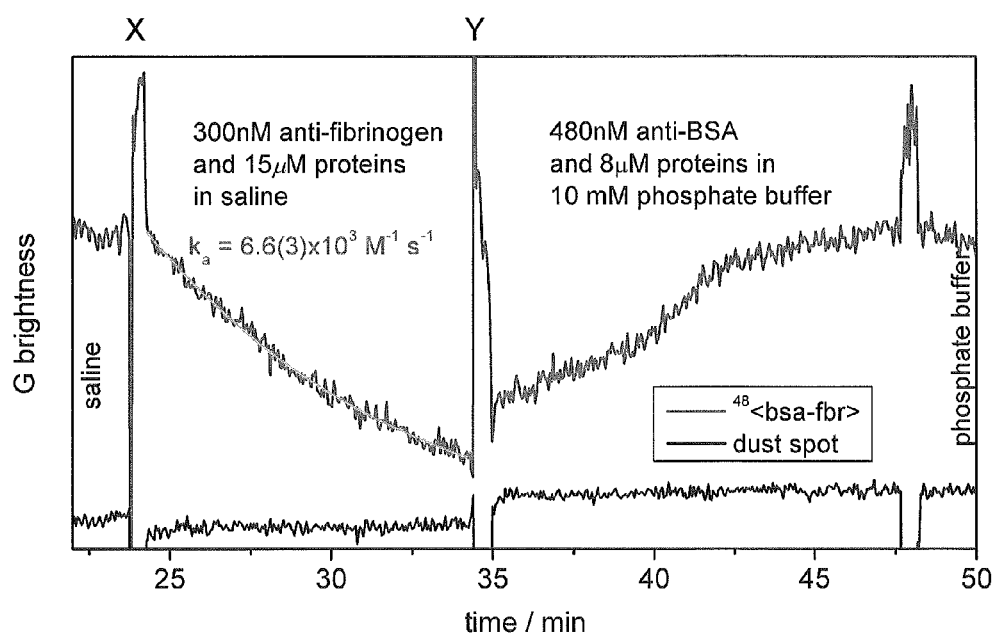

FIGS. 7a to 7c show similar data but for all the rows an in the array of FIG. 6a, this time the lower trace in FIG. 7c comprising a control spot. The measured refractive index sensitivity for this proof-of-principle experiment was $9 \times 10^{-4}$ RIU without the control spot and $2.2 \times 10^{-4}$ RIU with the control spot.

Figure 8A:
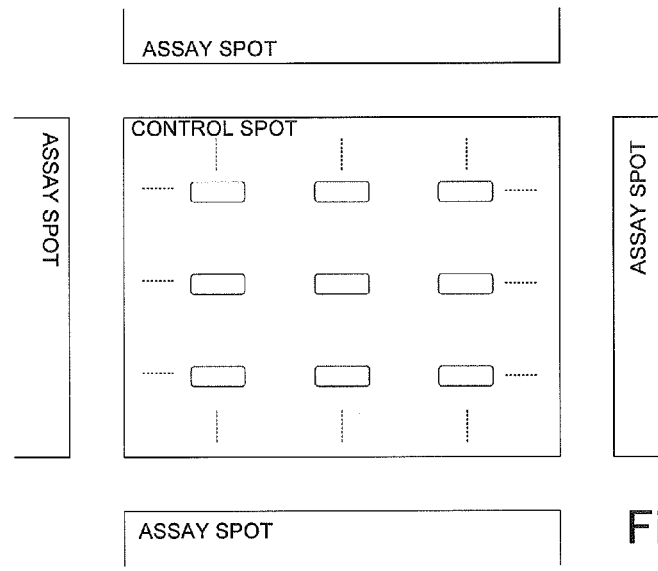
FIGS. 8a and 8b show, respectively, a schematic illustration of a part of a control spot for a plasmon-resonance based biosensor comprising a regular array (grid) of conductive elements, and a graph showing changes in relative brightness of the control spot with time as a range of different fluids are flushed over the control spot, illustrating refractive index sensitivity to bulk refractive index.
Figure 8B:
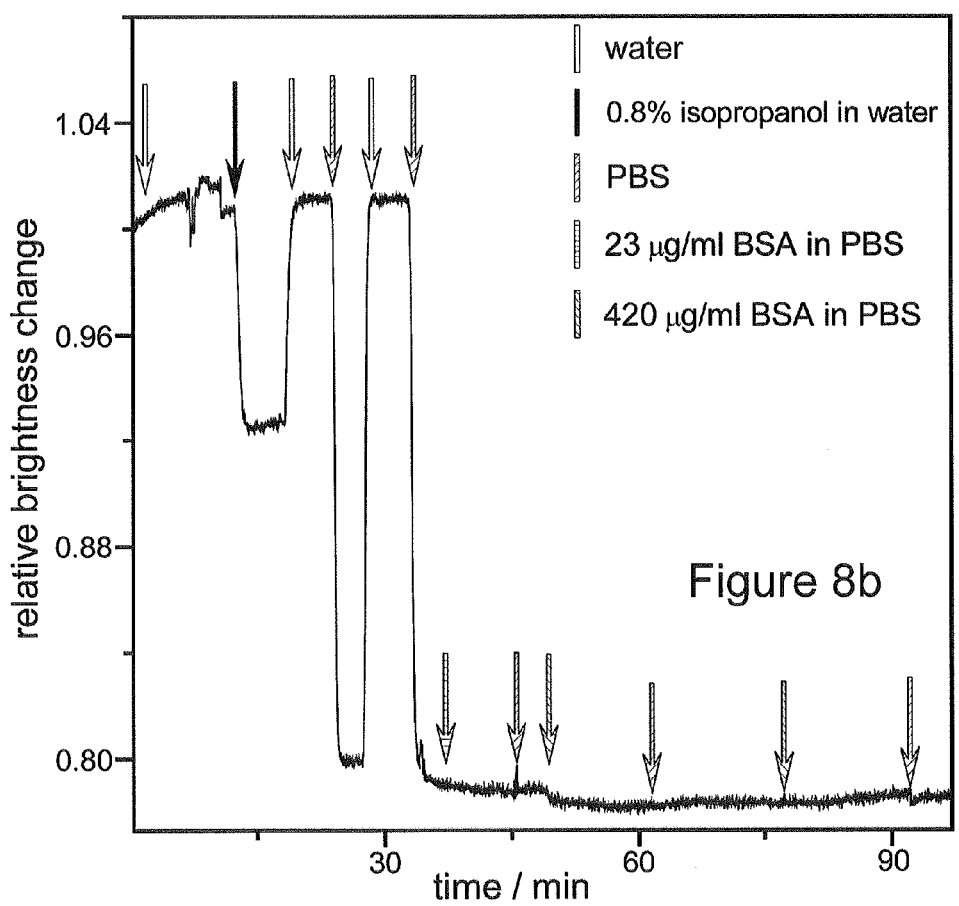

Referring now to FIG. 8a, this shows a control spot comprising a configuration of regularly spaced conductive elements (30×70 nm) constructed from electron-beam lithography, in a regular array of pitch 400 nm. When illuminated in the near-field configuration of the array reader shows sensitivity to changes in the bulk refractive index of $1 \times 10^{-5}$, demonstrated by the switch in organic solvent and from water to phosphate buffered saline shown in FIG. 8b.

When viewed normal to the surface there is no change in the scattered radiation intensity and therefore does not show sensitivity to binding proteins onto the gold surface and in this regard it is a useful control spot for bulk compositional changes.

A control spot sensitive substantially only to bulk refractive index has the following advantages in array design: The refractive index of a blood sample is dominated by the protein load and the bulk refractive index sensor spot can provide a direct measure of blood refractive index and composition. The overall protein load determines the kinetics of non-specific binding so a bulk refractive index determination enables the non-specific binding rate to be predicted. The bulk refractive index can act as a bench-mark for all assay spots.

Apparent binding rates constants for each assay on each spot may vary from spot to spot depending on the non-specific binding. Averaging over the total repeats of the assay on the array produces an empirical rate of binding for the target analyte. The empirical rate may be scaled by the bulk refractive index to correctly estimate the contribution from non-specific binding. This will inform the confidence in the extracted concentration of the target analyte. The preparation of, say a, blood sample prior to analysis may therefore include addition of other reagents. Variation of the bulk composition may be monitored for composition changes including the addition of the correct (desired) sample modifying agents.

It is believed that the mechanism is broadly as follows: each of the conductive elements of the control spot acts as a coherent source, resulting in interference in the light emitted by the surface plasmons excited in these conductive elements. The array of conductive elements thus generates an interference or fringe pattern and for a control spot of order 100 μm by 100 μm (FIG. 8a shows a portion of such a control spot) between 10 and 15 fringes are experimentally observed within the spot. These fringes move and change contrast as fluid flows over the control spot and the separation of the fringes is apparently dependent on the bulk refractive index of the fluid only, or at least this appears to dominate any surface effects at the control spot. Preferably the conductive elements form a regular array, although this is not essential. In general the assay spots of the biosensor are expected to show sensitivity to non-specific binding and thus it is important to be able to calibrate this out. It is believed that this non-specific binding has a rate constant which is proportional to the bulk refractive index or bulk protein load, and hence an empirical rate constant may be determined which is dependent on the total protein load. This can then be employed to correct the signals from the assay spots so that changes in the signals from the assay spots can be determined as due to detection of a desired target. More particularly the rate constant of binding to an assay spot may be calibrated and then from this rate constant a biomarker concentration may be determined.

The ability to calibrate in this way is useful as it significantly simplifies operation of the apparatus and compensation for bulk fluid properties, for example in the case of blood, blood thickness or changes in composition due to recent eating or drinking. This type of approach can also be employed if it is felt desirable to add a buffer to the fluid, for example blood, to inhibit non-specific binding since the amount of buffer may be effectively monitored using the control spot or spots.

Thus we have described a plasmon resonance-based biosensing microarray which in embodiments employs discrete islands of conductive nanoparticles and which, in embodiments, is viewed in a dark-field scattering arrangement, preferably at two wavelengths one to either side of the resonant peak, preferably with at least some of the spots being used as controls. This combination of features enables a combination of both very high sensitivity and also selectivity, more particularly discrimination against non-specific binding events. By following binding kinetics of a plurality of targets over time using such a microarray a characteristic fingerprint of a condition may be obtained based upon a multi-dimensional data set comprising time series data indicative of binding kinetics for a plurality of characterising targets. This multi-dimensional data may be fitted to one or more corresponding templates to identify the condition with a high degree of accuracy and sensitivity.

Thus further aspects of the invention provide methods and apparatus to perform such an identification of a condition by fitting multi-dimensional data, in particular from a plasmon resonance-based biosensing microarray as described above.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A biosensor array for Plasmon resonance-based sensing of a plurality of different biological targets simultaneously, the array comprising a transparent substrate having a surface bearing a plurality of assay spots for Plasmon resonance sensing, each of said assay spots comprising a discrete metallic island, said metallic island comprising a plurality of metallic nanoparticles to which are attached functionalizing molecules for binding to said biological target, different said islands being different said functionalizing molecules for binding to different ones of said biological targets, and wherein total internal reflection of light at said surface at a wavelength at or near said plasmon resonance results in scattering of said light away from said surface, said scattering being modulated by said binding of said biological targets;

wherein said metallic islands of said array are spaced apart, arranged at intervals of at least 0.1 mm on a non-conducting substrate, and wherein within said metallic island, said plurality of metallic nanoparticles comprise a discontinuous layer of individual, multi-faceted nanoparticles.

2. The biosensor array as claimed in claim 1, wherein said metallic nanoparticles have at least one dimension of less than 30 nm, and comprise rod-like nanoparticles.

3. The biosensor array as claimed in claim 1, wherein said nanoparticles include nanoparticles forming an optical antenna for said light, wherein said optical antenna comprises an adjacent pair of nanoparticles having a generally rod-like or triangular shape, and having adjacent ends separated by a gap of less than 50 nm, said nanoparticles having physical lengths which are resonant for said plasmon resonance at substantially the same optical wavelength.

4. The biosensor array as claimed in claim 1, further comprising at least one control spot substantially lacking said functionalizing molecules, and wherein said control spot comprises an array of metallic elements configured to produce an interference or fringe pattern when said control spot is viewed.

5. The biosensor array as claimed in claim 1, wherein said transparent substrate is configured as a Dove prism, and includes an edge or grating optical coupling for coupling said light into an edge of said transparent substrate of said array to waveguide said light within a thickness of said substrate.

6. The biosensor array as claimed in claim 1, wherein said metallic nanoparticles comprise gold nanoparticles, and wherein said different functionalizing molecules are attached to said metallic nanoparticles using the same ligand.

7. A method of using the biosensor array of claim 1 for a plasmon resonance-based sensing of a plurality of different biological targets simultaneously, the method comprising:
coupling light of at least one wavelength into said biosensor array such that total internal reflection of said light at said surface generates an evanescent wave field which excites plasmons in said functionalized metallic nanoparticles and scatters said light;
flowing a liquid carrying a plurality of said biological targets for analysis over said array;
imaging said scattered light from said array to generate image data for said biological targets carried by said liquid; and
analyzing said image data to determine levels of said biological targets carried by said liquid.

8. The method as claimed in claim 7, wherein said imaging of said scattered light comprises imaging said array from a side opposite to a side of said array being said assay spots.

9. The method as claimed in claim 7, wherein said imaging is performed in real-time to follow binding kinetics of said biological targets carried by said liquid, and wherein said analyzing comprises determining time variations of binding of said different targets to said different functionalizing molecules; and further comprising matching said time variations to one or more pathological conditions associated with said biological targets carried by said liquid.

10. The method as claimed in claim 7, wherein said light comprises light of at least two different wavelengths one to either side of said plasmon resonance, and wherein said analyzing includes forming a ratio of signals at said two different wavelengths in said image data.

11. The method as claimed in claim 7, wherein said analyzing comprises comparing a signal from one of said assay spots with a signal from another of said assay spots to compensate for non-specific binding interactions.

12. The method as claimed in claim 7, wherein said analyzing comprises controlling for a bulk refractive index of said liquid using a control spot substantially lacking said functionalizing molecules, wherein said control spot is configured to form a diffraction or interference pattern in said imaged scattered light, wherein said controlling uses said diffraction or interference pattern.

13. The method as claimed in claim 7, wherein said biosensor array has an open top onto which said liquid may be deposited, and one or more built-in semiconductor light sources configured to provide waveguided light within said transparent substrate of said array to excite said plasmons.

14. The method as claimed in claim 7, wherein said imaging comprises imaging dark-field scattered light through a back surface of said biosensor array.

15. The biosensor array as claimed in claim 1, further comprising an apparatus for plasmon resonance-based sensing of a plurality of different biological targets, the apparatus comprising:
means for coupling light of at least one wavelength into said biosensor array such that total internal reflection of said light at said surface generates an evanescent wave field which excites plasmons in said functionalized metallic nanoparticles and scatters said light;
means for flowing a liquid carrying a plurality of said biological targets for analysis over said array;
means for imaging said scattered light from said array to generate image data for said biological targets carried by said liquid; and
means for analyzing said image data to determine levels of said biological, targets carried by said liquid.

16. The biosensor array as claimed in claim 15, wherein said means for imaging comprises means to image dark-field scattered light through a back surface of said array.

17. The biosensor array as claimed in claim 1, further comprising an apparatus for reading the biosensor array for Plasmon resonance-based sensing for plasmon resonance-based sensing of a plurality of different biological targets, the array comprising a transparent substrate having a surface bearing a plurality of assay spots for plasmon resonance sensing, each of said assay spots comprising a discrete metallic island to which is attached functionalizing molecules for binding to said biological target, different said islands bearing different said functionalizing molecules for binding to different ones of said biological targets, and wherein total internal reflection of light at said surface at a wavelength at or near said plasmon resonance results in scattering of said light away from said surface, said scattering being modulated by said binding of said biological targets, the apparatus comprising:
a light source to generate light at two different substantially monochromatic wavelengths;
an optical coupling device to couple light from said light source into said sensing array;
an imaging system to image light from said array at said two different wavelengths scattered by plasmon resonance in said metallic islands, and to generate image date; and
an image analysis system coupled to said imaging system to receive said image data and to analyze said plasmon-resonance scattered light to determine levels of said different biological targets attached to said array.

18. The apparatus as claimed in claim 17, configured to determine said levels of said different biological targets attached to said array using light of two orthogonal polarizations.

19. A method of using the biosensor array of claim 1 for plasmon resonance-based sensing of different biological targets simultaneously, the method comprising:
coupling light of at least one wavelength into said biosensor array such that total internal reflection of said light at said surface generates am evanescent wave field which excites plasmons in said functionalized metallic nanoparticles, said light comprising polarized light with polarization modulation;

detecting an orientation of an elliptical of totally internally reflected modulated polarized light; and outputting a target sensing signal responsive to binding of said biological target to said functionalizing molecule dependent on detection of a change in said elliptical polarization orientation, wherein s- and p-polarization components of said polarized light do not self-interfere.

20. An apparatus for reading a plasmon resonance sensing array for plasmon resonance-based sensing of a plurality of different biological targets, the array comprising a transparent substrate having a surface being a plurality of assay spots for said plasmon resonance testing, the apparatus comprising:

a light source to generate polarized light;

a polarization modulator to modulate a polarization of said polarized light;

an optical system to illuminate said array with said modulated polarized light to generate plasmons in said assay spots by total internal reflection of said polarized light wherein s- and p-polarization components of said polarized light do not self-interfere;

a detection system to detect an orientation of an elliptical polarisation of said totally internally reflected modulated polarized light; and an output to output a target sensing signal dependent on binding of said biological target to said functionalizing molecule responsive to detection of a change in said elliptical polarization orientation;

and said plasmon resonance sensing array wherein each of said assay spots comprising a discrete metallic island, said metallic island comprising a plurality of metallic nanoparticles to which are attached functionalizing molecules for binding to said biological target, different said islands bearing different said functionalizing molecules for binding to different ones of said biological targets;

wherein said metallic islands of said array are spaced apart, arranged at intervals of at least 0.1 mm on a non-conducting substrate and wherein within said metallic island, said plurality of metallic nanoparticles comprise a discontinuous layer of individual, multi-faceted nanoparticles.

21. The apparatus as claimed in claim 20, wherein said polarization modulator is pixelated for separate interrogation of said assay spots, and wherein said detection system is configured to enable separation of signals from different ones of said assay spots.

22. The apparatus as claimed in claim 20, configured to image dark-field scattered light through a back surface of said array.

* * * * *